(12) United States Patent
Wahl et al.

(10) Patent No.: US 10,095,050 B2
(45) Date of Patent: Oct. 9, 2018

(54) METHOD, A SYSTEM AND A COMPUTER READABLE MEDIUM FOR OPTIMIZING AN OPTICAL SYSTEM, AND A METHOD OF EVALUATING ATTENTIONAL PERFORMANCE

(71) Applicant: Carl Zeiss Vision International GmbH, Aalen (DE)

(72) Inventors: Siegfried Wahl, Donzdorf (DE); Hamed Bahmani, Tuebingen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 5 days.

(21) Appl. No.: 15/368,378

(22) Filed: Dec. 2, 2016

(65) Prior Publication Data

US 2018/0157063 A1    Jun. 7, 2018

(51) Int. Cl.
| | | |
|---|---|---|
| G02C 7/02 | (2006.01) |
| G02B 27/00 | (2006.01) |
| A61B 3/00 | (2006.01) |
| G06F 17/50 | (2006.01) |

(52) U.S. Cl.
CPC ............ *G02C 7/028* (2013.01); *A61B 3/0025* (2013.01); *G02B 27/0012* (2013.01); *G02C 7/027* (2013.01); *G06F 17/5009* (2013.01)

(58) Field of Classification Search
CPC .... G02B 27/0012; G02C 7/028; G02C 7/027; G06F 17/5009
USPC ............ 351/159.76, 159.75, 159.74, 159.73, 351/159.01, 41
See application file for complete search history.

(56) References Cited

U.S. PATENT DOCUMENTS

| | | | |
|---|---|---|---|
| 6,019,470 A | 2/2000 | Mukaiyama et al. | |
| 6,747,646 B2 * | 6/2004 | Gueziec | A61B 6/032 345/420 |

OTHER PUBLICATIONS

Bahmani, H., Nasrabadi, A. M., and Gholpayeghani, M.R.H. (2008). Nonlinear data fusion in saliency-based visual attention. In 2008 4th International IEEE Conference Intelligent Systems, IS 2008, 327-330. doi:10.1109/IS.2008.4670416.

Barbero, S., and Portilla, J. (2016). The relationship between dioptric power and magnification in progressive addition lenses. Ophthalmic Physiol. Opt. 36, 421-427. doi:10.1111/opo.12301.

Carrasco, M. (2011). Visual attention: The past 25 years. Vision Res. 51, 1484-1525. doi:10.1016/j.visres.2011.04.012.

Cho, S.-G., Hwang, J.-J., and Kwak, N.-J. (2012). Visible Distortion Predictors Based on Visual Attention in Color Images. J. Inf. Commun. Converg. Eng. 10, 300-306. doi: 10.6109/jicce.2012.10. 3.300.

(Continued)

*Primary Examiner* — Tuyen Tra
(74) *Attorney, Agent, or Firm* — Walter Ottesen, P.A.

(57) ABSTRACT

A method of optimizing an optical system defined by at least one parameter, wherein the method includes steps of: a) determining, based on a first image without distortion, a second image with distortion introduced by the optical system, b) simulating human attention on the first image and the second image by using a computational model of visual attention, to obtain a simulated human attention on the both images, c) evaluating an attentional performance of the optical system based on the simulated human attention on both images, d) adjusting the at least one parameter of the optical system to improve the attentional performance.

15 Claims, 3 Drawing Sheets

(56) References Cited

OTHER PUBLICATIONS

Itti, L., and Koch, C. (2000). A saliency-based search mechanism for overt and covert shifts of visual attention. Vision Res. 40, 1489-1506. doi:10.1016/S0042-6989(99)00163-7.

Itti, L., and Koch, C. (2001). Computational modelling of visual attention. Nat. Rev. Neurosci. 2, 194-203. doi:10.1038/35058500.

Koch, C., and Ullman, S. (1985). Shifts in selective visual attention: towards the underlying neural circuitry. Hum. Neurobiol. 4, 219-27. doi:10.1016/j.imavis.2008.02.004.

Laurent Itti, Christof Koch, and E. N. (1998). A Model of Saliency-Based Visual Attention for Rapid Scene Analysis. IEEE Trans. Pattern Anal. Mach. Intell. 46, 883-885. doi: 978 0 7340 3893 7.

Logan, G. D. (1996). The Code theory of visual attention: an integration of space-based and object-based attention. Psychol. Rev. 103, 603-649. doi:10.1037/0033-295X.103.4.603.

Selenow, A., Bauer, E. a, Ali, S. R., Spencer, L. W., and Ciuffreda, K. J. (2002). Assessing visual performance with progressive addition lenses. Optom. Vis. Sci. 79, 502-5. doi: 10.1097/00006324-200208000-00012.

Sheedy, J. E., Burt, M., Bailey, I. L., Azus, J., and Borish, I. M. (1987). Optics of progressive addition lenses. Am. J. Optom. Physiol. Opt. 64, 90-99. doi: 10.1097/00006324-198702000-00003.

Vu, C. T., Larson, E. C., and Chandler, D. M. (2008). Visual fixation patterns when judging image quality: Effects of distortion type, amount, and subject experience. Proc. IEEE Southwest Symp. Image Anal. Interpret., 73-76. doi:10.1109/SSIAI.2008.4512288.

Faubert, J. "The Influence of Optical Distortions and Transverse Chromatic Aberration on Motion Parallax and Stereopsis in Natural and Artificial Environments." Three-Dimensional Television, Video and Display Technologies (2002): 359.

C. Guillox, H. De Rossi, G. Marin, B. Bourdoncle, M. Hernandez, L. Calixte, and F. Karioty, "The importance of the ophthalmic progressive lens shape on the space perception," in Proceedings of the European Academy of Optometry and Optics Meeting, Dublin, Ireland, Apr. 20-22, 2012.

Adams, W. J., Banks, M. S., and Van Ee, R. (2001). Adaption to three-dimensional distortions in human vision. Nat. Neurosci. 4, 1063-1064. doi:10.1038/nn729.

Barbero, S., and Portilla, J. (2015). Geometrical interpretation of dioptric blurring and magnification in ophthalmic lenses. Opt. Express 23, 13185-13199. doi:10.1364/OE.23.013185.

De Fez, M. D., Luque, M. J., and Viqueira, V. (2002). Enhancement of contrast sensitivity and losses of chromatic discrimination with tinted lenses. Optom. Vis. Sci. 79, 590-597. doi:10.1097/00006324-200209000-00010.

Desimone, R., and Duncan, J. (1995). Neural mechanisms of selective visual attention. Annu. Rev. Neurosci. 18, 193-222. doi:10.1146/annurev.ne. 18.030195.001205.

\* cited by examiner

METHOD, A SYSTEM AND A COMPUTER READABLE MEDIUM FOR OPTIMIZING AN OPTICAL SYSTEM, AND A METHOD OF EVALUATING ATTENTIONAL PERFORMANCE

FIELD OF THE INVENTION

The present invention relates to optics, specifically relates to a method, a system and a computer readable medium for optimizing an optical system, and a method of evaluating attentional performance.

BACKGROUND OF THE INVENTION

Spectacles can distort the visual world in a number of ways. Progressive and multifocal lenses impose substantial geometric distortion on the peripheral vision as a price for a wide, distortion-free clear view in the center (Selenow et al., 2002). In progressive addition lenses (PAL) the mean curvature of the optical surface varies gradually along a region called intermediate vision corridor to provide variable optical power for the eye (Sheedy et al., 1987). Around this area the PAL unavoidably introduces some undesired optical effects like blurring, non-uniform magnification, that is, distortion, and image displacement (Barbero and Portilla, 2016). These effects cause impairments in visual perception, including space (Guilloux et al., 2012) and depth (Faubert, 2002). Image distortions can also alter the performance of subjects in visual search tasks (Vu et al., 2008, Cho et al., 2012). This could be due to subjective changes in perceived quality of images, or objective changes in saliency of objects which may render them less conspicuous to the eye.

Despite the widely shared belief in the general public that 'we see everything around us', only a small fraction of the information registered by the visual system reaches levels of processing that mediate perception and directly influence behavior (Itti and Koch, 2000). Attention is the key to this process that turns looking into seeing by a selective mechanism (Carrasco, 2011). This selection process can be feature-based, space-based or object-based (Logan, 1996) and essentially optimizes the use of the system's limited resources by enhancing the representations of the relevant locations or features of the visual environment against less relevant items.

The ability to orient vision rapidly towards salient objects in cluttered scenes has evolutionary significance because it allows the animal to detect quickly prey and predators in the visual world. In the modern human era, we are not concerned much about predators, but our daily life and social interactions rely heavily on a rapid and reliable visual processing. Impairment of a fast pre-attentive mechanism for visual search has fatal implications in situations like driving, where rapid reaction to visual stimuli is important. If a stimulus is sufficiently salient, it will pop out of a visual scene. A salient stimulus for a driver can be other moving vehicles, pedestrians running onto the road, or traffic signs and warnings. The speed of this saliency-based form of attention is on the order of 25 to 50 milliseconds per item (Itti and Koch, 2001) which is sufficiently fast for tasks like driving. Volitional deployment of attention is slower—200 milliseconds or—more but can operate in parallel.

However, in the current optical system configuration method, the influence of the optical system on the attentional performance is not considered.

SUMMARY OF THE INVENTION

The present invention aims to optimize the optical system to improve the attentional performance. Models of visual attention, saliency, awareness or consciousness are integrated into optical configuration or opto-mechanical configurations of optical or digital-optical systems.

According to one aspect of the invention, there is provided a method of optimizing an optical system defined by at least one parameter, wherein the method comprises steps of:
a) determining, based on a first image without distortion, a second image with distortion introduced by the optical system,
b) simulating human attention on the first image and the second image by using a computational model of visual attention, to obtain a simulated human attention on both images,
c) evaluating an attentional performance of the optical system based on the simulated human attention on both images,
d) adjusting the at least one parameter of the optical system to improve the attentional performance.

Preferably, the computational model of visual attention is a computational model of bottom-up visual attention.

Preferably, in step c), the attentional performance of the optical system is evaluated based on a performance evaluation metric for the computational model of visual attention.

Preferably, in step d), the at least one parameter of the optical system is adjusted to reduce a difference between the performance evaluation metrics of the first image and the second image.

Preferably, the optical system comprises at least one of: a lens, in particular a spectacle lens, a microscope, a camera, an ophthalmic device, a virtual reality device, a microsurgery device or an illumination device.

Preferably, the distortion introduced by the optical system is at least one distortion selected from a group consisting of: a geometric distortion, a color change, a motion-blurred distortion, an intensity change, a noise, a compression distortion, an astigmatism, and an aberration.

Preferably, the optical system comprises a lens, and wherein, the attentional performance is incorporated into a lens configuration optimization process.

Preferably, in step a), the second image is determined based on a distortion map of the optical system.

According to another aspect of the invention, there is provided a method of evaluating an attentional performance of a human eye with a disease, wherein the method comprises steps of:
a) determining, based on a first image without distortion, a second image with distortion introduced by the disease,
b) simulating human attention on the first image and the second image by using a computational model of visual attention, to obtain a simulated human attention on both images,
c) evaluating the attentional performance of the human eye based on the simulated human attention on both images.

Preferably, the computational model of visual attention is a computational model of bottom-up visual attention.

Preferably, in step c), the attentional performance of the optical system is evaluated based on a performance evaluation metric for the computational model of visual attention.

According to another aspect of the invention, there is provided a system of optimizing an optical system defined by at least one parameter, the system comprising:
a determining module, configured to determine, based on a first image without distortion, a second image with distortion introduced by the optical system,
a simulating module, configured to simulate human attention on the first image and the second image by using a computational model of visual attention, to obtain a simulated human attention on both images, an evaluating module, configured to evaluate an attentional performance of the optical system based on the simulated human attention on both images, an adjusting module, configured to adjust the at least one parameter of the optical system to improve the attentional performance.

Preferably, the evaluating module is further configured to evaluate the attentional performance of the optical system based on a performance evaluation metric for the computational model of visual attention.

Preferably, the adjusting module is configured to adjust the at least one parameter of the optical system to reduce a difference between the performance evaluation metrics of the first image and the second image.

According to another aspect of the invention, a computer readable medium storing computer-readable instructions is provided that, when executed, causes a computer to implement steps of:

a) determining, based on a first image without distortion, a second image with distortion introduced by an optical system defined by at least one parameter, b) simulating human attention on the first image and the second image by using a computational model of visual attention, to obtain a simulated human attention on both images, c) evaluating an attentional performance of the optical system based on the simulated human attention on both images, d) adjusting the at least one parameter of the optical system to improve the attentional performance.

According to an embodiment of the invention, it is important for the optimization of optical system configuration in order to minimize their negative effects on attention for wearers especially in critical situations like driving.

According to another embodiment of the invention, it can also give a recommendation to people with certain levels of distortion in the form of any of the early visual features through predictive simulations, whether they are able to meet adequate level of performance required for tasks with high levels of attentional demand. For example for patients having cataracts, blur effects can be simulated and a recommendation can be given based on the method of the present invention for example whether they can drive.

BRIEF DESCRIPTION OF THE DRAWINGS

The invention will now be described with reference to the drawings wherein.

DESCRIPTION OF THE PREFERRED
EMBODIMENTS OF THE INVENTION

Embodiments of the present application are described herein in detail and shown by way of example in the drawings. It should be understood that, although specific embodiments are discussed herein there is no intent to limit the scope of the invention to such embodiments. To the contrary, it should be understood that the embodiments discussed herein are for illustrative purposes, and that modified and alternative embodiments may be implemented without departing from the scope of the invention. Similarly, specific structural and functional details disclosed herein are merely representative for purposes of describing the embodiments. The invention described herein, however, may be embodied in many alternate forms and should not be construed as limited to only the embodiments set forth herein.

Figure 1:
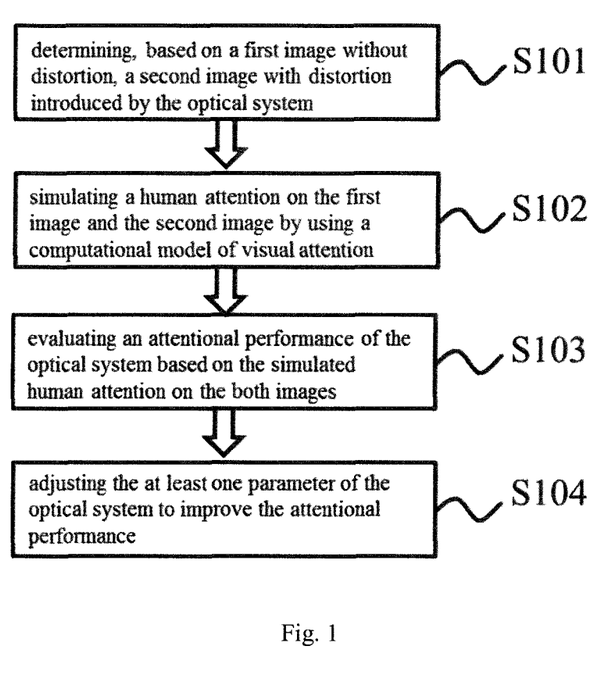
FIG. 1 is a flow chart of a method according to an embodiment of the present invention.

FIG. 1 shows a flow chart of the method of optimizing an optical system defined by at least one parameter according to an embodiment of the present invention.

In an embodiment of the present invention, the optical system comprises at least one of: a lens, in particular a spectacle lens, a microscope, a camera, an ophthalmic device, a virtual reality device, a microsurgery device or an illumination device.

The parameter may be a set of physical parameters from a production perspective and considered as independent parameters. These parameters are for example radius of a lens (or other optical element such as mirrors or prisms), form (such as aspheres and freeform), distance between optical elements, thickness, material, coating et cetera.

As seen from FIG. 1, in step S101, a second image with distortion introduced by the optical system is determined based on a first image without distortion.

In an embodiment of the present invention, the distortion introduced by the optical system is at least one distortion selected from a group consisting of: a geometric distortion, a color change, a motion-blurred distortion, an intensity change, a noise, a compression distortion, an astigmatism, and an aberration.

The second image can be determined based on the at least one parameter of the optical system. In an embodiment of the present invention, the second image can be simulated according to tinted filters used in a lens or the digital transformation of an image in an opto-digital system. In another embodiment of the present invention, the second image is determined based on a distortion map of the optical system, for example, a distortion map of a lens that can be obtained based on the at least one parameter of the optical system according to any known method or other method developed in the future.

In step S102, human attention on the first image and the second image is simulated by using a computational model of visual attention, to obtain a simulated human attention on both images.

The most important function of selective visual attention is to direct our gaze as fast as possible to objects of interest in our visual environment. For the selection of one particular spatial location being accomplished much evidence has accumulated in favor of a two-component framework for the control of where in a visual scene attention is deployed: a bottom-up, fast, and image-based mechanism that biases the observer towards selecting stimuli based on their saliency, and a second slower, top-down mechanism, which directs the 'spotlight of attention' under voluntary control and uses task-dependent cues.

The computational model of visual attention of the present invention is a model developed to predict or simulate human attention upon looking at an image. The computational model of visual attention may be a computational model of bottom-up visual attention or a computational model of top-down visual attention. Since the top-down visual attention is highly dependent on the internal state of the observer and depends on factors like observer history which is very difficult to quantify and model, it is preferable to use a computational model of bottom-up visual attention in the following embodiment to elaborate the present invention.

Specifically, in the following, a model of saliency-based visual attention (saliency model for rapid scene analysis Itti, Koch (1998)) is adopted in one embodiment of the present invention. Those skilled persons should understand that any known model can be adopted instead or in combination with each other, for example a feature-based model, a space-based model, object-based model, a sustained model, a deep gaze model, a cognitive model, an information theory based model, a spectral analysis based model, a graph based model, a machine learning based model. It can also be any model developed in the future to predict or simulate human attention, awareness and consciousness. They can be linear or non-linear, analytical or numerical, statistical, deterministic, generative or combinations of all of these, for example, pre-trained deep-learning algorithms showed very good performance in saliency prediction.

Koch and Ullman (1985) introduced the idea of a saliency map to accomplish pre-attentive selection. A saliency map is an explicit two-dimensional map that encodes the saliency of visual objects in the environment purely based on the low-level visual attributes of the object, and is independent of the nature of the particular task; although it can be influenced by contextual, figure—ground effects (Itti, Koch, 1998). Competition among neurons in this map gives rise to a single winning location that corresponds to the most salient object, which constitutes the next target. If this location is subsequently inhibited, the system automatically shifts to the next most salient location. This internal dynamic models the saccadic eye movements in visual search.

In one embodiment of the present invention, the extent to which multiple distortion sources affect the saliency of objects in a visual search task is addressed. The distortion source is at least one distortion selected from a group consisting of: a geometric distortion, a color change, a motion-blurred distortion, an intensity change, a noise, a compression distortion, an astigmatism, and an aberration. Other distortions that are not mentioned here may also be covered by the independent claim of the present invention, as long as they are caused by the optical system.

In the model of, for example, Laurent Itti, Christof Koch, and Ernst Niebur (1998) for rapid image analysis, inspired by the behavior and the neuronal architecture of the early primate visual system, multi-scale image features are combined into a single topographical saliency map. A dynamical neural network then selects attended locations in order of decreasing saliency.

According to a preferred embodiment of the present invention, in the optimization of optical systems (for example spectacle lens, intraocular lens) an explicit two-dimensional map (or three or more dimensional maps) is incorporated. The two-dimensional map encodes the saliency of visual objects in the environment based, for example, on the low-level visual attributes of the object, and is independent of the nature of the particular task; although it can be influenced by contextual, figure—ground effects. This allows optimization to the natural seeing or to enhanced seeing for distinct tasks (for example driving, office, sport). That means particular tasks can be taken into account. The model can also take higher-level features into account.

In step S103, an attentional performance of the optical system is evaluated based on the simulated human attention on both images.

In one embodiment of the present invention, the attentional performance of the optical system is evaluated based on a performance evaluation metric for the computational model of visual attention. The performance evaluation metrics can be any known metrics used for evaluating the computational model of visual attention or other metrics developed in the future to evaluate the computational model of visual attention.

In one embodiment of the present invention, a performance measure similar to Bahmani et al., 2008 to quantify the effects of distortion on any of the features that contribute to saliency in the model can be used. Counting the number of false detections before hitting the target in the computational model of saccadic eye movements during the search for a traffic sign for example could be a performance indicator. The effect of such distortions on the performance of the model in detecting the target traffic sign is noticeable. Therefore models of visual attention, saliency, awareness or consciousness should be integrated into optical configuration or opto-mechanical configurations of optical or digital-optical systems.

In one embodiment of the present invention, the attentional performance of the optical system is evaluated based on a simulated visual search task driven by bottom-up visual attention mechanism. This could be especially important for eyewear and lens designers to minimize the effect of optical distortions on visual attention.

In step S104, the at least one parameter of the optical system is adjusted to improve the attentional performance.

In one embodiment of the present invention, the at least one parameter of the optical system is adjusted to reduce a difference between the performance evaluation metrics of the first image and the second image.

The ultimate goal can be "as close as possible to the natural seeing behavior" or in specific applications an enhanced seeing behavior, superior to the natural seeing behavior (for example, in surgical microscopes a specific seeing behavior, deviating from the natural, could be beneficial).

In a preferred embodiment of the present invention, the optic system comprises a lens, in particular a spectacle lens. The attentional performance is incorporated into a lens configuration optimization process.

Figure 2:
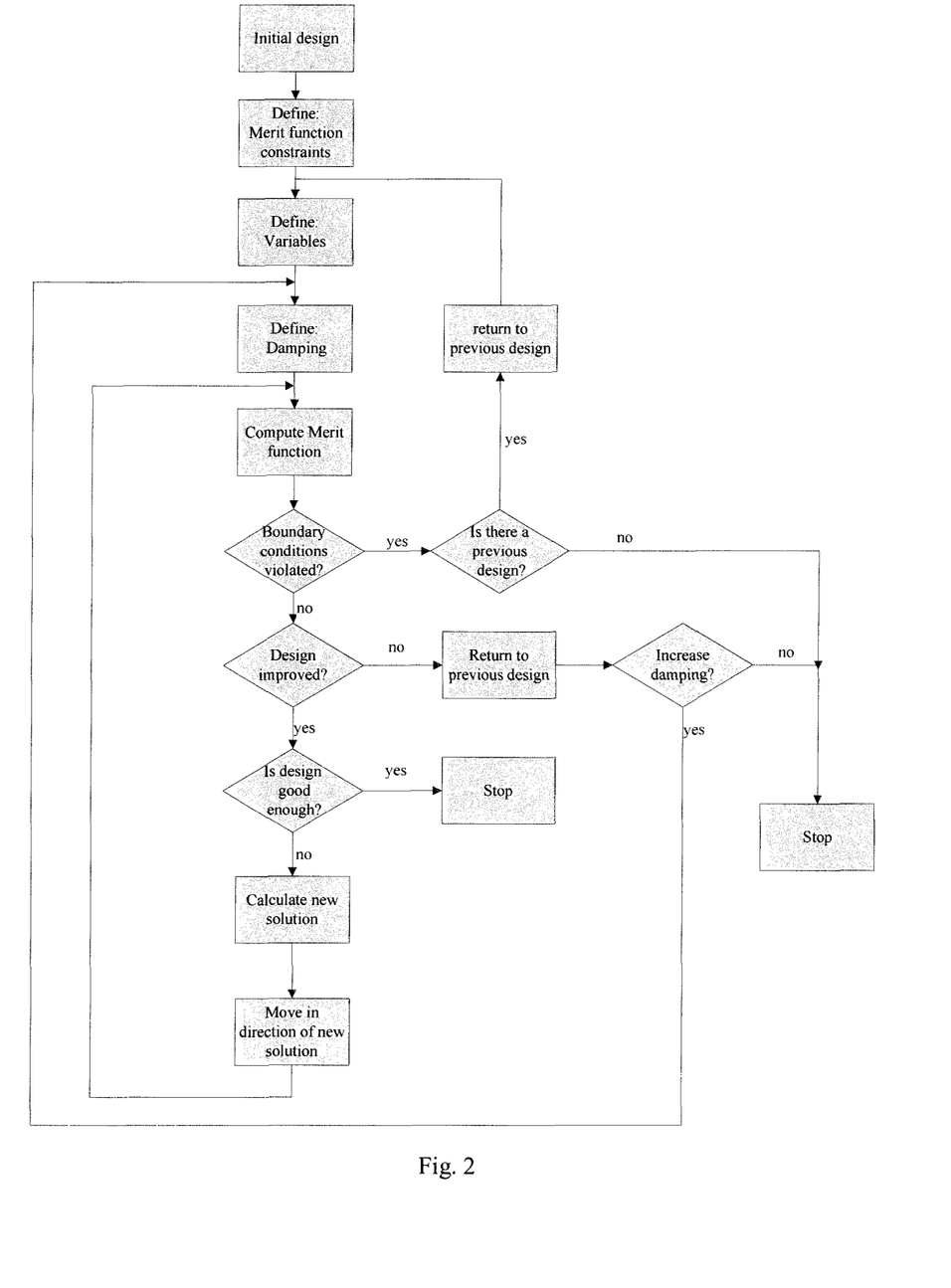
FIG. 2 is a flow chart of a typical lens configuration program according to state of the art.

FIG. 2 shows a typical process of a lens configuration optimization according to the state of the art. No saliency/attention/awareness/consciousness is included.

According to a preferred embodiment, the realization of the method proposed in this invention can be carried out on every level of the known optical configuration optimization process, for example, it could be incorporated in the performance criteria, for example, in the merit function as a statistical deviation of the natural behavior. But it could also be introduced in the tolerance process, for example in the step of determining whether boundary conditions are violated or in the step of determining whether the system is good enough as shown in FIG. 2.

The skilled person should understand, according to the present invention, that by incorporating the attentional performance into the optimization process among other parameters such as root mean square (RMS), modulation transfer function (MTF), point spread function (PSF), optical transfer function (OTF), spot radius, centroid, astigmatism, distortion, aberrations, and transmission, it is possible that better attentional performance may be achieved at the cost of sacrificing other properties, for example, MTF.

In one embodiment, independent production parameters are adjusted to reach certain levels of attentional performance as target values. Alternatively, in another embodiment, independent parameters are adjusted to reach a certain level of MTF et cetera and evaluate the attentional performance according to the proposed method, and if it was not good, go back to the optimization algorithm and adjust again the production parameters or set the performance measures targets like MTF to reach the desired attentional performance.

The parameters to be adjusted are for example radius of a lens (or other optical element such as mirrors or prisms), form (such as aspheres and freeform), distance between optical elements, thickness, material, coating et cetera.

In another embodiment of the present invention, the modeling works also for color and disturbance of saliency through influence of color by the optical system. The method of the present invention could also be used for color optimization (for example clarity, sunglasses, ski goggles) in the lens configuration optimization or vision simulation. The method proposed in the present invention can also work together with aberration optimization.

The method according to the present invention is also applicable in the configuration process of contact lenses, intraocular lenses, microscopes, surgical microscopes et cetera, every optics where attention processes are playing a role including, for example, augmented reality, virtual reality, heads up displays. It can be used to improve the camera of an autonomous driving system. It could even be implemented in the configuration of illumination systems as well to mimic the natural seeing behavior with distinct illumination systems (for example, reflectors or spotlight for car driving, office illumination, lamp configuration, which LED/LCD/OLED should be used, et cetera). In one embodiment of the invention, the method is used to again obtain or simulate images with particular lighting systems (headlamps of cars for example) and measure the attentional performance and optimize the configuration (for example, LED or Halogen lamp et cetera or the angle of the lamps et cetera) in order to get better attentional performance.

Optimization is not the only case in which the methods presented herein can be used; the methods can also be used simply to simulate vision through eyeglasses or other optics. That means the methods can be used also in vision simulators or optometric and ophthalmic devices.

Figure 3:
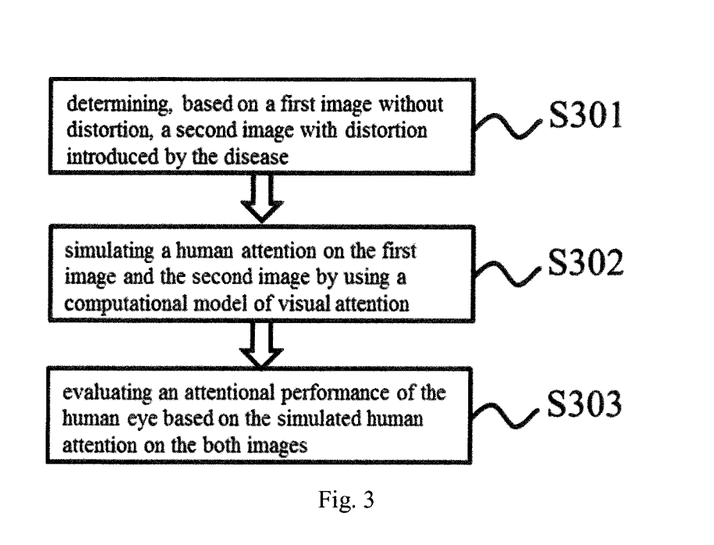
FIG. 3 is a flow chart of a method according to another aspect of the present invention; and, FIG. 4 is a structural diagram of a system according to an embodiment of the present invention.

FIG. 3 shows a flow chart of a method of evaluating an attentional performance of a human eye with a disease according to another aspect of the present invention.

In step S301, a second image with distortion introduced by the disease is determined based on a first image without distortion.

In an embodiment of the present invention, the second image is determined with the help of medical or ophthalmic devices.

In step S302 human attention on the first image and the second image is simulated by using a computational model of visual attention, to obtain a simulated human attention on both images.

In step S303, the attentional performance of the human eye is evaluated based on the simulated human attention on the both images.

According to an embodiment of the invention, it can also give a recommendation to people with certain levels of distortion in the form of any of the early visual features through predictive simulations, whether they are able to meet an adequate level of performance required for tasks with high levels of attentional demand. For example for patients having cataracts, blur effects can be simulated and a recommendation can be given based on the method of the present invention for example whether they can drive.

In a preferred embodiment of the present invention, the computational model of visual attention is a computational model of bottom-up visual attention.

In a preferred embodiment of the present invention, the attentional performance of the optical system is evaluated based on a performance evaluation metric for the computational model of visual attention.

Figure 4:
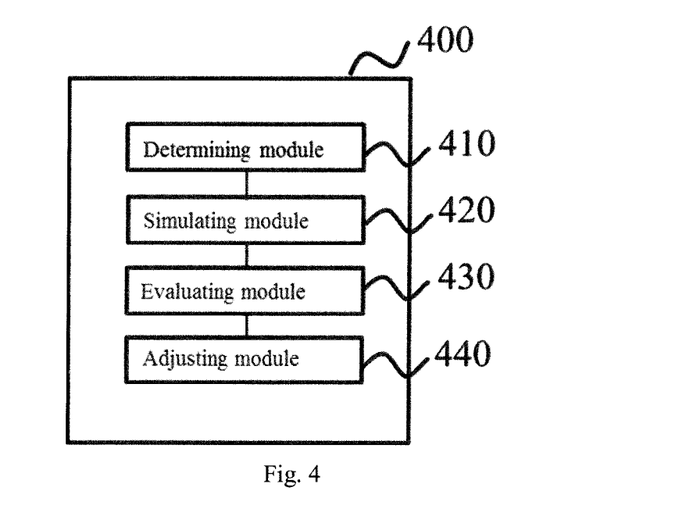

FIG. 4 shows a system (400) of optimizing an optical system defined by at least one parameter, the system comprising:

a determining module (401), configured to determine, based on a first image without distortion, a second image with distortion introduced by the optical system, a simulating module (402), configured to simulate human attention on the first image and the second image by using a computational model of visual attention, to obtain a simulated human attention on the both images, an evaluating module (403), configured to evaluate an attentional performance of the optical system based on the simulated human attention on both images, an adjusting module (404), configured to adjust the at least one parameter of the optical system to improve the attentional performance.

According to another aspect of the invention, a computer readable medium storing computer-readable instructions is provided that, when executed, causes a computer to implement steps of:

a) determining, based on a first image without distortion, a second image with distortion introduced by an optical system defined by at least one parameter, b) simulating a human attention on the first image and the second image by using a computational model of visual attention, to obtain a simulated human attention on the both images, c) evaluating an attentional performance of the optical system based on the simulated human attention on the both images, d) adjusting the at least one parameter of the optical system to improve the attentional performance.

The computer readable medium can, for example, be a non-transitory computer readable storage medium.

It is understood that the foregoing description is that of the preferred embodiments of the invention and that various changes and modifications may be made thereto without departing from the spirit and scope of the invention as defined in the appended claims.

LIST OF REFERENCES

Bahmani, H., Nasrabadi, A. M., and Gholpayeghani, M. R. H. (2008). Nonlinear data fusion in saliency-based visual attention. in 2008 4th International IEEE Conference Intelligent Systems, IS 2008, 327-330. doi:10.1109/IS.2008.4670416.

Barbero, S., and Portilla, J. (2016). The relationship between dioptric power and magnification in progressive addition lenses. Ophthalmic Physiol. Opt. 36, 421-427. doi: 10.1111/opo.12301.

Carrasco, M. (2011). Visual attention: The past 25 years. Vision Res. 51, 1484-1525. doi:10.1016/j.visres.2011.04.012.

Cho, S.-G., Hwang, J.-J., and Kwak, N.-J. (2012). Visible Distortion Predictors Based on Visual Attention in Color Images. J. Inf. Commun. Converg. Eng. 10, 300-306. doi:10.6109/jicce.2012.10.3.300.

Itti, L., and Koch, C. (2000). A saliency-based search mechanism for overt and covert shifts of visual attention. Vision Res. 40, 1489-1506. doi:10.1016/50042-6989(99)00163-7.

Itti, L., and Koch, C. (2001). Computational modelling of visual attention. Nat. Rev. Neurosci. 2, 194-203. doi: 10.1038/35058500.

Koch, C., and Ullman, S. (1985). Shifts in selective visual attention: towards the underlying neural circuitry. Hum. Neurobiol. 4, 219-27. doi:10.1016/j.imavis.2008.02.004.

Laurent Itti, Christof Koch, and E. N. (1998). A Model of Saliency-Based Visual Attention for Rapid Scene Analysis. IEEE Trans. Pattern Anal. Mach. Intell. 46, 883-885. doi: 978 0 7340 3893 7.

Logan, G. D. (1996). The CODE theory of visual attention: an integration of space-based and object-based attention. Psychol. Rev. 103, 603-649. doi:10.1037/0033-295X.103.4.603.

Selenow, A., Bauer, E. a, Ali, S. R., Spencer, L. W., and Ciuffreda, K. J. (2002). Assessing visual performance with progressive addition lenses. Optom. Vis. Sci. 79, 502-5. doi: 10.1097/00006324-200208000-00012.

Sheedy, J. E., Buri, M., Bailey, I. L., Azus, J., and Borish, I. M. (1987). Optics of progressive addition lenses. Am. J. Optom. Physiol. Opt. 64, 90-99. doi:10.1097/00006324-198702000-00003.

Vu, C. T., Larson, E. C., and Chandler, D. M. (2008). Visual fixation patterns when judging image quality: Effects of distortion type, amount, and subject experience. Proc. IEEE Southwest Symp. Image Anal. Interpret., 73-76. doi:10.1109/SSIAI.2008.4512288.

Faubert, J. "The Influence of Optical Distortions and Transverse Chromatic Aberration on Motion Parallax and Stereopsis in Natural and Artificial Environments." Three-Dimensional Television, Video, and Display Technologies (2002): 359.

C. Guilloux, H. de Rossi, G. Marin, B. Bourdoncle, M. Hernandez, L. Calixte, and F. Karioty, "The importance of the ophthalmic progressive lens shape on the space perception," in Proceedings of the European Academy of Optometry and Optics Meeting, Dublin, Ireland, 20-22 Apr. 2012.

What is claimed is:

1. A method of optimizing an optical system defined by at least one parameter, wherein the method comprises steps of:
   a) determining, based on a first image without distortion, a second image with distortion introduced by the optical system,
   b) simulating human attention on the first image and the second image by using a computational model of visual attention, to obtain a simulated human attention on both images,
   c) evaluating an attentional performance of the optical system based on the simulated human attention on both images,
   d) adjusting the at least one parameter of the optical system to improve the attentional performance.

2. The method of claim 1, wherein, the computational model of visual attention is a computational model of bottom-up visual attention.

3. The method of claim 1, wherein, in step c), the attentional performance of the optical system is evaluated based on a performance evaluation metric for the computational model of visual attention.

4. The method of claim 3, wherein, in step d), the at least one parameter of the optical system is adjusted to reduce a difference between the performance evaluation metrics of the first image and the second image.

5. The method of claim 1, wherein, the optical system comprises at least one of: a lens, a microscope, a camera, an ophthalmic device, a virtual reality device, a microsurgery device or an illumination device.

6. The method of claim 1, wherein, the distortion introduced by the optical system is at least one distortion selected from a group consisting of: a geometric distortion, a color change, a motion-blurred distortion, an intensity change, a noise, a compression distortion, an astigmatism, and an aberration.

7. The method of claim 1, wherein, the optical system comprises a lens, and wherein, the attentional performance is incorporated into a lens configuration optimization process.

8. The method of claim 1, wherein, in step a), the second image is determined based on a distortion map of the optical system.

9. A method of evaluating an attentional performance of a human eye with a disease, wherein the method comprises steps of:
   a) determining, based on a first image without distortion, a second image with distortion introduced by the disease,
   b) simulating human attention on the first image and the second image by using a computational model of visual attention, to obtain a simulated human attention on the both images,
   c) evaluating the attentional performance of the human eye based on the simulated human attention on the both images.

10. The method of claim 9, wherein, the computational model of visual attention is a computational model of bottom-up visual attention.

11. The method of claim 9, wherein, in step c), the attentional performance of the optical system is evaluated based on a performance evaluation metrics for the computational model of visual attention.

12. A system of optimizing an optical system defined by at least one parameter, the system comprising:
    a determining module, configured to determine, based on a first image without distortion, a second image with distortion introduced by the optical system,
    a simulating module, configured to simulate human attention on the first image and the second image by using a computational model of visual attention, to obtain a simulated human attention on both images,
    an evaluating module, configured to evaluate an attentional performance of the optical system based on the simulated human attention on both images,
    an adjusting module, configured to adjust the at least one parameter of the optical system to improve the attentional performance.

13. The system of claim 12, wherein, the evaluating module is further configured to evaluate the attentional performance of the optical system based on a performance evaluation metric for the computational model of visual attention.

14. The system of claim 13, wherein, the adjusting module is configured to adjusted the at least one parameter of the optical system to reduce a difference between the performance evaluation metrics of the first image and the second image.

15. A non-transitory computer readable medium storing computer-readable instructions that, when executed, cause a computer to implement steps of:

a) determining, based on a first image without distortion, a second image with distortion introduced by an optical system defined by at least one parameter,
b) simulating human attention on the first image and the second image by using a computational model of visual attention, to obtain a simulated human attention on both images,
c) evaluating an attentional performance of the optical system based on the simulated human attention on both images,
d) adjusting the at least one parameter of the optical system to improve the attentional performance.

* * * * *

UNITED STATES PATENT AND TRADEMARK OFFICE
CERTIFICATE OF CORRECTION

PATENT NO. : 10,095,050 B2
APPLICATION NO. : 15/368378
DATED : October 9, 2018
INVENTOR(S) : Wahl et al.

It is certified that error appears in the above-identified patent and that said Letters Patent is hereby corrected as shown below:

On the Title Page

Under (57) Abstract: delete "a simulated human attention on the both" and substitute -- "a simulated human attention on both -- therefor.

On Page 2:
Under (56) References cited, other publications: delete "Burt, M.," and substitute -- Buri, M., -- therefor.

In the Specification

In Column 7:
Line 27: delete "heads up" and substitute -- heads-up -- therefor.

In Column 9:
Line 3: delete "doi: 10.1016/50042-6989(99)" and substitute -- doi: 10.1016/S0042-6989(99) -- therefor.

In the Claims

In Column 10:
Line 28: delete "the" after "attention on".

In Column 10:
Line 31: delete "the" after "attention on".

In Column 10:
Line 38: delete "metrics" and substitute -- metric -- therefor.

Signed and Sealed this
Fourth Day of June, 2019

Andrei Iancu
*Director of the United States Patent and Trademark Office*